US00PP31615P3

(12) United States Plant Patent
Probasco et al.

(10) Patent No.: US PP31,615 P3
(45) Date of Patent: Mar. 31, 2020

(54) HOP PLANT NAMED 'HBC 586'

(50) Latin Name: *Humulus lupulus*
Varietal Denomination: HBC 586

(71) Applicant: HOP BREEDING COMPANY, L.L.C., Yakima, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 16/350,341

(22) Filed: Nov. 1, 2018

(65) Prior Publication Data

US 2019/0166748 P1 May 30, 2019

Related U.S. Application Data

(60) Provisional application No. 62/707,472, filed on Nov. 3, 2017.

(51) Int. Cl.
*A01H 5/02* (2018.01)
*A01H 6/00* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 5/02
See application file for complete search history.

*Primary Examiner* — Annette H Para
(74) *Attorney, Agent, or Firm* — Svendsen Legal, LLC

(57) ABSTRACT

A new hop plant named 'HBC 586' is disclosed. 'HBC 586' is used for its exceptional and unique aromatic qualities.

4 Drawing Sheets

Genus and species: *Humulus lupulus*.
Variety denomination: 'HBC 586'.

STATEMENT REGARDING FEDERALLY SPONSORED RESEARCH OR DEVELOPMENT

None

BACKGROUND OF THE INVENTION

'HBC 586' is a product of a controlled breeding program carried out by the inventors in the Yakima Valley of Washington State. 'HBC 586' was one of several seedlings resulting from a controlled cross made in 2007 with female parent 'YCR 21' (unpatented) and male parent '01239-2' (unpatented). Seedling plants from this cross were planted in 2008 and screened for disease resistance and sex in a greenhouse and field nursery near Toppenish, Wash. A single plant of 'HBC 586' was selected in 2010. In 2011 'HBC 586' was expanded by asexual tissue culture propagation to 7 plants in an evaluation block near Toppenish, Wash. In 2017 'HBC 586' was further expanded by asexual tissue culture propagation to a 1 acre test block near Toppenish, Wash. The 'HBC 586' plants have now been observed and evaluated for several years. Throughout several generations of asexual propagation, 'HBC 586' has been observed to retain its distinctive characteristics and remain true to type.

COMPARISON OF 'HBC 586' TO PARENT PLANT AND COMPARISON CULTIVAR

Table 1. below, sets forth some of the distinguishing characteristics of 'HBC 586' as compared to its female parent 'YCR 21', and to the 'Cascade' cultivar as a closely comparable cultivar.

TABLE 1

| | INSTANT CV. 'HBC 386' | FEMALE PARENT 'YCR 21' | COMPARISON CV. 'CASCADE' |
|---|---|---|---|
| Alpha (% of cone weight) | 12.5-13 | 12.5-16 | 5.5-9 |
| Beta (% of cone weight) | 7.5-8 | 3.8-4.7 | 6-7.5 |
| Co-humulone (% of alpha acids) | 26-30 | 33.5-37 | 30-35 |
| Total Oil (mL/100 g) | 2.2-2.8 | not available | 1.0-2.5 |
| Aroma Profile | Mango, Orange, Pepper | not available | Grapefruit, Spice, Pine |

BRIEF DESCRIPTION OF THE PHOTOGRAPHS

Figure 1:
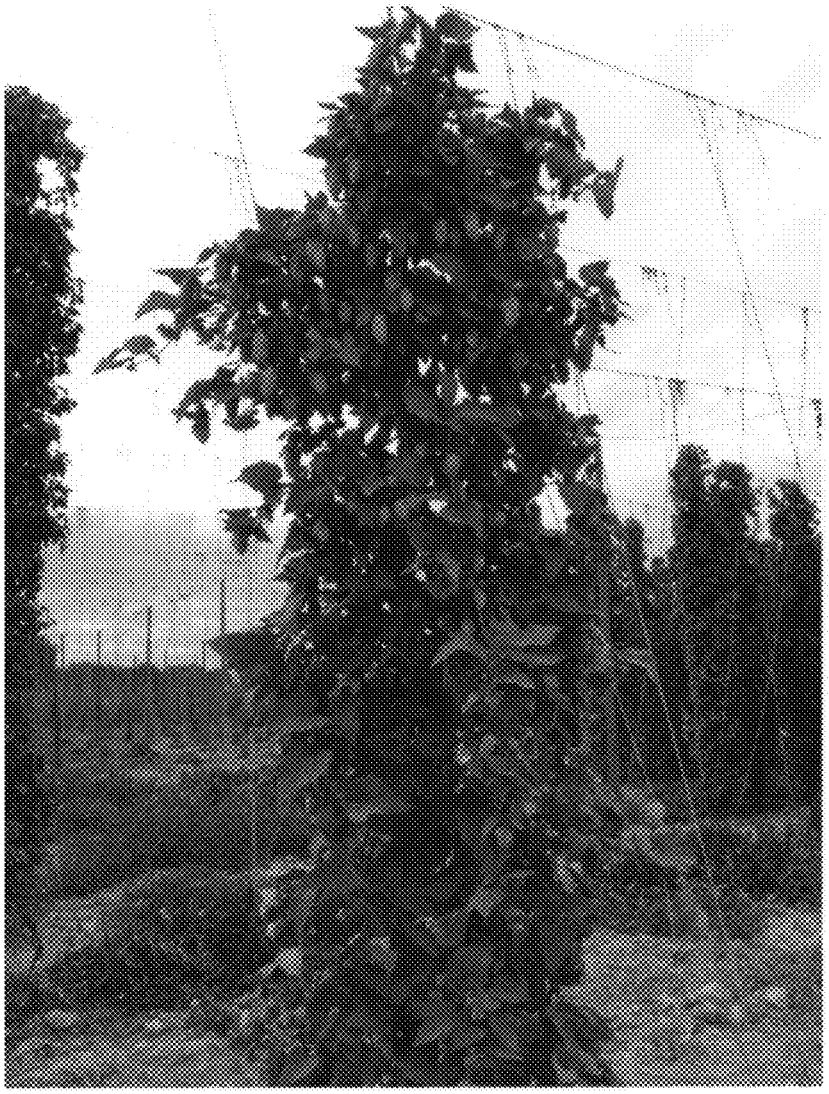
FIG. 1 illustrates a mature 'HBC 586' hop plant grown on a trellis.
Figure 2:
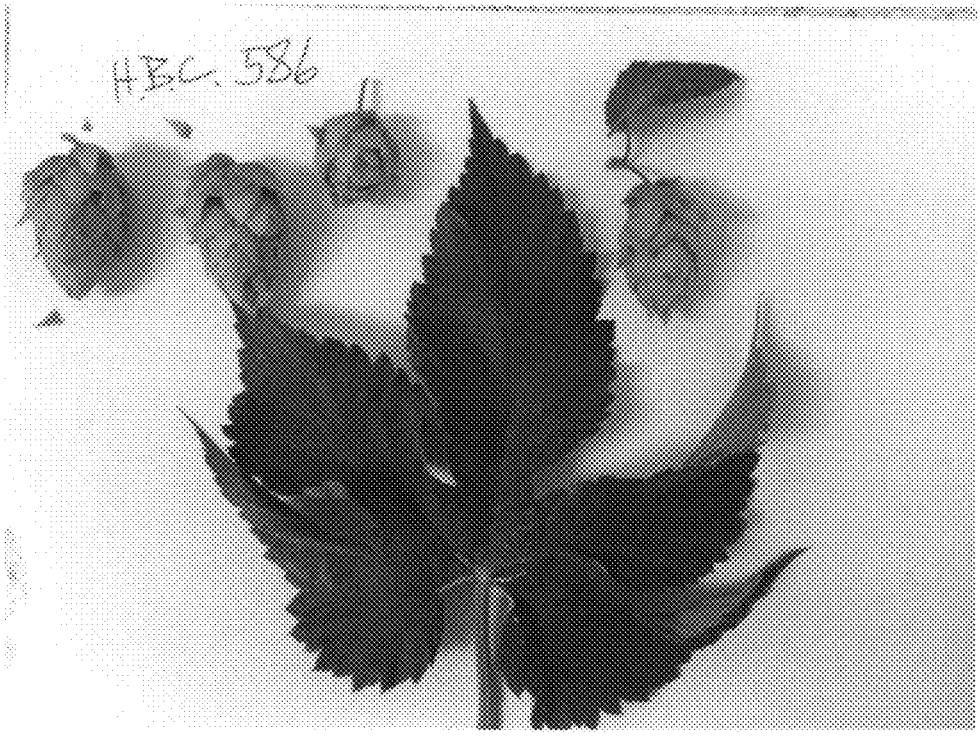
FIG. 2 illustrates whole cones and a leaf of the 'HBC 586' hop plant.
Figure 3:
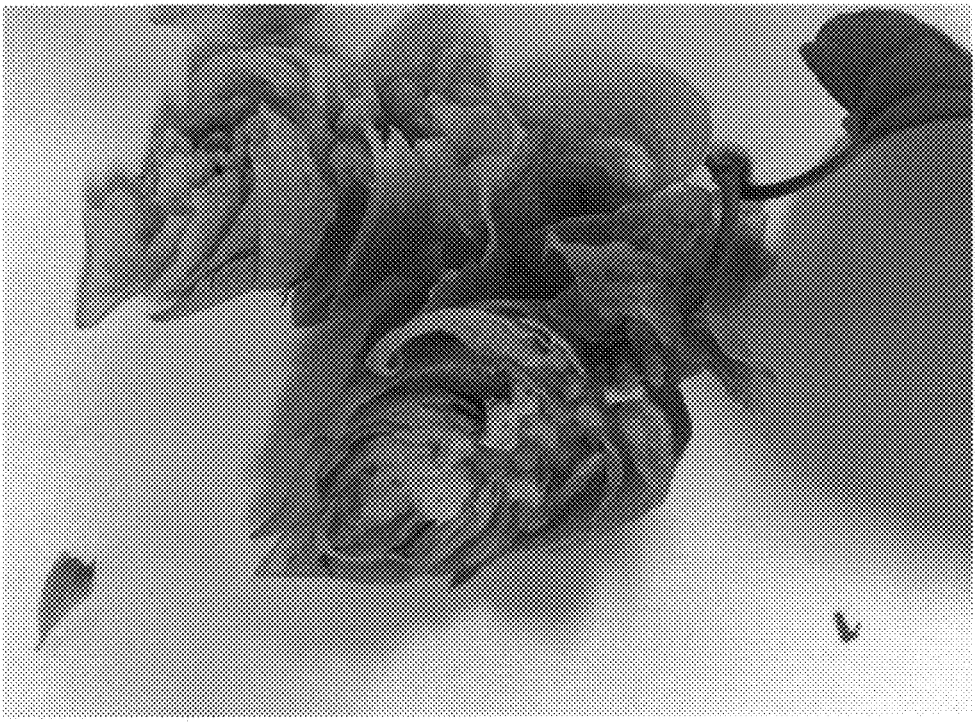
FIG. 3 illustrates cross-sectioned cones of the 'HBC 586' hop plant.
Figure 4:
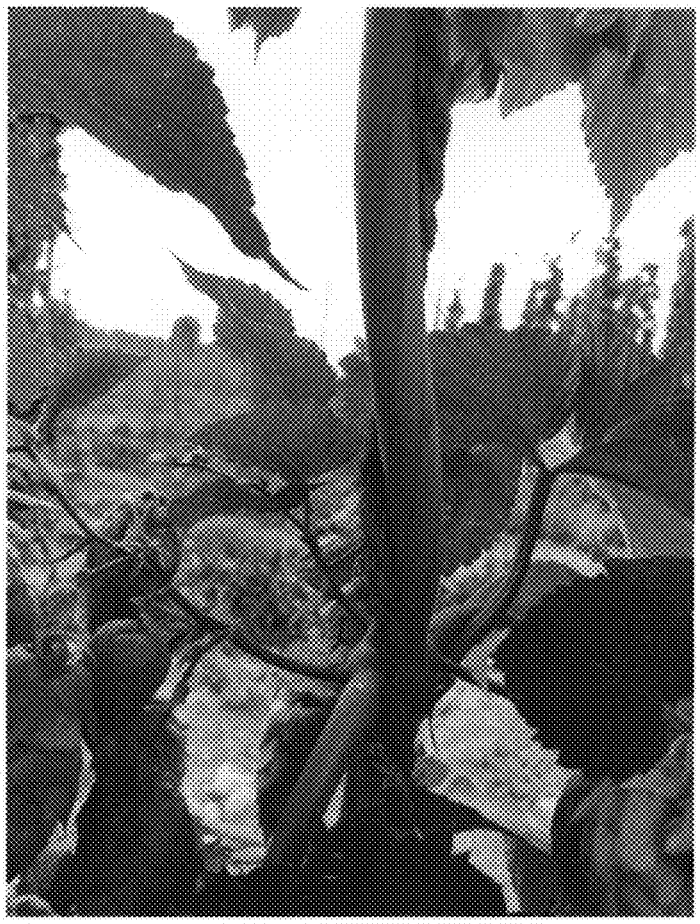
FIG. 4 illustrates a bine on the mature 'HBC 586' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2015-2017 growing seasons at Toppenish, Wash.

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.

Sex: Female.

Use: Brewing beer and ale.

Harvest date: September 1st to 14th (during 2011 to 2017 growing seasons at Toppenish, Wash.).

Yield: Average yield is 1800 to 2500 kg/hectare.

Plant shape: Climbing bine, cylindrical growth.

Disease reaction: Powdery Mildew — Tolerant.

Time of flowering: Mid to Late July.

Oil analytical characteristics (averages):

| | |
|---|---|
| % Alpha Acid (% cone weight) | 12.5 to 13% |
| % Beta Acid (% cone weight) | 7.5 to 8% |
| % Cohumulone (% alpha acids) | 26 to 30% |
| Total Oil (ml/100 g of cones): | 2.2 to 2.8% Oil |
| Hop Storage Index | <28% |

Bine:

*Bine color.*—146D.
*Stripe present.*—Yes.
*Stripe color.*—152A.
*Stipule direction.*—Up.
*Stipule color.*—145A.
*Bine diameter.*—9.1 mm at base; 10.3 mm at nine feet; and 6.3 mm at terminal end of eighteen feet.
*Anthocyanin coloration on main bine.*—Medium.
*Average lateral length* (*on middle third of plant*).—80 cm.
*Average laterals length* (*on upper third of plant*).—80 cm.
*Lateral density* (*on middle third of plant*).—Medium (two laterals per node).

Leaf:

*Arrangement.*—Opposite.
*Shape.*—Palmate.
*Average length of mature leaf.*—11.9 cm.
*Average width of mature leaf.*—12.3 cm.
*Color of mature leaf upper surface.*—139A.
*Color of mature leaf lower surface.*—137A.
*Number of lobes.*—5.
*Margin.*—Serrate.
*Serrations per inch.*—5 (typically).
*Average petiole length* (*of mature leaf*).—95 mm.
*Average petiole diameter* (*of mature leaf*).—3 mm to 4 mm.
*Petiole color at base.*—146D.
*Venation.*—Palmate.
*Vein color.*—146C.

Cone:

*Avg. length.*—46 mm.
*Avg. diameter.*—18 mm.
*Bract tip color.*—145D.
*Bract base color.*—141A.
*Bracteole color.*—149D.
*Cone shape.*—Oblong.
*Bract shape.*—Cuspidate.
*Bract tip shape.*—Caudate.
*Bract tip position.*—Alternating.
*Bracteole shape.*—Obtuse.
*Bracteole length.*—17 mm.
*Bracteole width.*—12 mm.
*Lupulin glands shape.*—Peduncutlated oblong polyps.
*Lupulin glands number per cone.*—Moderate to many.
*Lupulin glands color.*—9A.

The invention claimed is:

1. A new and distinct Hop plant as illustrated and described herein.

* * * * *